United States Patent [19]

Shibayama et al.

[11] Patent Number: 5,057,324

[45] Date of Patent: Oct. 15, 1991

[54] KALLIKREIN INHIBITOR SUBSTANCE, A PROCESS FOR PREPARATION AND PHARMACEUTICAL COMPOSITIONS THEREOF

[75] Inventors: Yoji Shibayama; Yoshio Toyomaki, both of Katoh, Japan

[73] Assignee: Nippon Zoki Pharmaceutical Co., Ltd., Osaka, Japan

[21] Appl. No.: 221,975

[22] Filed: Jul. 20, 1988

[30] Foreign Application Priority Data

Jul. 23, 1987 [JP] Japan ................................ 62-184981

[51] Int. Cl.$^5$ ..................... A61K 35/12; A61K 35/36
[52] U.S. Cl. ..................... 424/520; 424/570; 424/571; 424/572; 424/574; 424/558; 424/559; 424/557; 424/553; 424/548; 424/563; 424/568; 424/529; 424/573
[58] Field of Search ................ 424/95, 520, 571, 572; 574/21

[56] References Cited

FOREIGN PATENT DOCUMENTS

| 0101515 | 9/1978 | Japan | 424/95 |
| 0130502 | 10/1979 | Japan | 514/21 |
| 55-28943 | 2/1980 | Japan . | |
| 0118711 | 7/1984 | Japan | 424/95 |

OTHER PUBLICATIONS

Imai et al., "Inhibition of the Release of Gradykinin--Like Substances into the Perfusate of Rat Hind Paw by Neurotropin", Jpn. J. Pharmacol. 36(1):104–106 (1984); CA101:144825.

*Primary Examiner*—Douglas W. Robinson
*Assistant Examiner*—Jean C. Witz
*Attorney, Agent, or Firm*—Armstrong, Nikaido, Marmelstein, Kubovick & Murray

[57] ABSTRACT

A physiologically active substance is extracted from infected tissues inoculated with a poxvirus. The novel substance of the present invention has inhibitory action against the formation of kallikrein, thus is useful as drugs such as antiinflammatory, analgesic and antiallergic agents.

8 Claims, No Drawings

KALLIKREIN INHIBITOR SUBSTANCE, A PROCESS FOR PREPARATION AND PHARMACEUTICAL COMPOSITIONS THEREOF

BACKGROUND OF THE INVENTION

The invention relates to a physiologically active substance extracted from infected tissues, a process for preparation and pharmaceutical compositions thereof.

As a result of investigations for a physiologically active substance extracted from infected tissues, which is produced by inoculation with a poxvirus to animal's tissues, organs or cultured cell, the inventors have found that a novel physiologically active substance having inhibitory action against the formation of kallikrein and a process for preparation thereof.

An object of the present invention is to provide a novel physiologically active substance extracted from infected tissues. Another object of the invention is to provide a process for preparation of the substance. A further object of the invention is to provide pharmaceutical compositions containing the physiologically active substance.

DETAILED DESCRIPTION OF THE INVENTION

A process for preparing the physiologically active substance of the present invention comprises extracting from infected tissues inoculated with a poxvirus; deproteinizing the extract; mixing the deprotenized extraction with an adsorbent; eluting the adsorbed material from adsorbent; and fractionating the eluted based on molecular weight. That is to say, 1) The infected tissues are homogenized with an extraction medium, and tissue fragments are removed. 2) The extracted solution thus obtained is subjected to the removal treatment of proteins. 3) An adsorbent is added to the deproteinized solution, and then the material adsorbed to the adsorbent is eluted. 4) The eluted material is further fractionated based on molecular weight to give the substance of the present invention.

The present invention is described in detail hereinafter.

The term "infected tissues" used in the specification of the present invention means "animal's tissues, organs or cultured cell inoculated or infected with a poxvirus".

A poxvirus, for example, orthopoxvirus such as vaccinia virus, cowpox virus, variola virus, infectious ectromelia virus or monkeypox virus, parapoxvirus such as orf virus, paravaccinia virus or bovine papular stomatitis virus, capricopoxvirus such as sheeppox virus, goatpox virus or lumpy skin disease virus, avipoxvirus such as fowlpox virus or hare fibroma virus, leporipoxvirus such as rabbit myxoma virus or rabbit fibroma virus, swinepoxvirus, Yaba monkey tumor virus or Tarapox virus, can be used.

To obtain the infected tissues, various kinds of animals or birds can be utilized, for example, rabbit, sheep, goat, pig, cow, horse, monkey, hamster, guinea pig, rat, mouse or hen can be employed. The animal or bird can be selected according to a specie of poxvirus and other conditions. Also any kind of cultured cell, in which the selected poxvirus can multiply, is available, for example, cultured cell or tumor cell of kidney, skin, lung, testis, liver, muscle, adrenal, thyroid gland, brain, nerve cell or blood cell of rabbit, sheep, goat, pig, cow, horse, monkey, hamster, guinea pig, rat, mouse, hen or their embryo, cultured cell derived from human such as Hela cell, or decidua of the hatching egg can be employed.

The infected tissues are collected under aseptic conditions and ground to as small a size as possible. An extraction medium is added to the ground material and it is homogenized. As an extraction medium, distilled water, physiological saline, weakly acidic or basic buffer etc. is available, and if desired, a stabilizer such as glycerin, a disinfectant or preservative such as phenol, or inorganic salt such as sodium chloride, potassium chloride or magnesium chloride can be added to the medium. At that time, the extraction can be facilitated by a procedure to disintegrate cell tissues, such as freeze-thaw extraction, sonication, treatment with a detergent or an enzyme dissolving cell membrane.

The resulting emulsion is filtered or centrifuged to remove tissue fragments. The filtrate or supernatant is subjected to removal treatment of proteins, which can be carried out according to a known method, for example, heating, sonication, treatment with a protein-denaturant such as an acid, a base, urea, guanidine, an organic solvent or a detergent, iso-electric point precipitation or salting-out technique. Subsequently, the denatured proteins thereby precipitated is removed by filtration using a filter paper such as cellulose or nitrocellulose, a glass filter, sellaite, Seitz's filter etc., ultrafiltration, gel filtration, ion-exchange chromatography or centrifugation.

The resulting extract containing the active substance is made acidic, preferably pH 3.5–5.5, by addition of an acid such as hydrochloric acid, sulfuric acid or hydrobromic acid, and then subjected to adsorption to an adsorbent such as active carbon, kaolin or ion-exchange resin. The adsorbent can be added to the extracted solution and it is stirred, or the extracted solution can be passed through a column of the adsorbent.

To elute the material containing the active substance of the present invention, a basic solution is added to the adsorbent, preferably adjusted the suspension to pH 9–12, and then the mixture is incubated or stirred at room temperature or at a suitable temperature above room temperature by heating. The elution is achieved by removing the absorbent according to a known method such as filtration or centrifugation. After the eluate is adjusted to near neutral by addition of an acid, fractionation based on molecular weight such as ultrafiltration or gel filtration is carried out to give the active substance of the present invention.

EXAMPLE

The following examples, which are illustrative only and not intended to limit the scope of the invention, describe the preparation of the physiologically active substance of the present invention.

EXAMPLE 1

Vaccinia virus was inoculated to the skin of healthy adult rabbit. The inflamed skin was cut off under aseptic conditions and well ground. Aqueous phenol solution was added to this ground material and subjected to homogenization, and the emulsion was filtered by centrifugation. The resulting filtrate was adjusted to pH 4.8–5.5, and then heated in a stream of 100° C. steam. After removing proteins thereby precipitated by filtration, the filtrate was adjusted to near pH 9 by addition of sodium hydroxide, heated at 100° C. and filtered. The filtrate was adjusted to pH 4.5 and 7.5% active carbon was added thereto. After stirring for 4.5 hrs, the suspension was filtered. Water was added to the resulting active carbon and the suspension was adjusted to pH 10.9 by addition of sodium hydroxide. The extraction procedure was carried out by stirring for 1.5 hrs at 60° C. The suspension was filtered to remove the active carbon. The filtrate was adjusted to near pH 8 by addition of hydrochloric acid and concentrated to dryness under reduced pressure. The residue was dissolved in distilled water and an insoluble matter was removed by filtration. Subsequently, the solution was filtered through a ultrafiltration membrane eliminating substances molecular weight of which is more than 20,000. To the remaining solution concentrated to small amount, distilled water was added and it was filtrated again. The procedure was repeated several times. Next the resulting filtrate, which was containing substances molecular weight of which is less than 20,000, was subjected to ultrafiltration again using a membrane removing substances molecular weight of which is more than 1,000 in the same manner as mentioned above to give the substance of the present invention, which did not pass the membrane.

EXAMPLE 2

The extract prepared in the same deproteinizing process as Example 1 was adjusted to pH 3.8 and 15% active carbon was added thereto. After stirring for 5 hrs, the suspension was filtered. To the resulting active carbon, aqueous solution of sodium hydroxide (pH 11.5) was added and the suspension was stirred for 3 hrs at 45° C. The active carbon was removed by filtration. The filtrate was neutralized and subjected to the ultrafiltration procedures, which was carried out in the same manner as Example 1, to give the physiologically active substance of the present invention.

The substance of the invention thus obtained was concentrated to dryness under reduced pressure. As a result of weighing the dried substance, the yield of the substance of the present invention is 0.5–1.0 g when 1 kg of infected skin-tissues of mature rabbit are employed.

The physical and chemical properties of the physiologically active substance obtained in the above examples are as follows.
1) Appearance: Pale yellowish brown and hygroscopic powder.
2) Solubility:
   Soluble in water, methanol and acetone.
   Insoluble in benzene and ether.
3) Acidity: The pH of aqueous solution thereof is pH 6.5–7.5.
4) Molecular weight: greater than 1,000 but less than 20,000
5) Ultraviolet adsorption: $\lambda max = 265$–$275$ nm.
6) Color reaction:
   Positive; amino acid, sugar, phosphorus.
   Negative; protein, phenol.

The following descriptions serve to illustrative pharmaceutical studies of the substance of the present invention.

(1) Inhibitory action against the formation of kallikrein

Kallikrein is a group of proteinase widely distributed in the plasma and tissues of various kinds of animals. Inactive prekallikrein is converted into active kallikrein through an activation of blood coagulation factor XII. The inhibitory action of the substance of the present invention against the formation of kallikrein was assayed according to the method described in Example 1 of European Patent Publication No.0259857. That is, in the primary reaction, kaolin suspension was added to the human plasma diluted with physiological saline. After a certain while, Lima Bean trypsin inhibitor was added to terminate the activation of kallikrein. In the second reaction, the amount of kallikrein formed in the primary reaction was measured by the use of a synthetic substrate specific to kallikrein, such as D-Pro-Phe-Arg-p-nitroaniline. In the above reaction system, the activity of the test substance to inhibit the formation of kallikrein was measured by mixing the test substance with the human plasma prior to addition of kaolin suspension.

An example of the results is shown in Table 1.

TABLE 1

| Test substance | $IC_{50}$ ($\mu$g/ml)* |
| --- | --- |
| Substance of the invention | 58 |
| Ketoprofen | 700 |

*$IC_{50}$ = Concentration 50% inhibiting the formation of kallikrein

Kallikrein acts upon kininogen to liberate kinins such as bradykinin, hence the liberation of kinins is depressed by inhibition of the formation of kallikrein. As can be seen from Table 1, the substance of the present invention has excellent inhibitory action against the formation of kallikrein. The inhibitory action of the substance is superior to that of Ketoprofen analgesic action of which is partly due to the inhibitory action against the liberation of bradykinin. In addition the substance of the present invention showed a remarkable effect intravenously on carrageenan or sodium urate crystal induced paw edema in rats.

Although the results are not shown herein, other fraction than the substance of the present invention, which is fractionated by ultrafiltration, had scarcely shown the inhibitory action against the formation of kallikrein.

Kinins such as bradykinin have various physiological actions, for example, enhancement of vascular permeability, contraction of smooth muscles, development of pain and hypotensive action, thus are playing an important role for function control in living bodies. As stated earlier, the inhibition of the formation of kallikrein suggests the inhibition of kinins liberation, therefore, the physiologically active substance of the present invention having remarkable inhibitory action against the formation of kallikrein is extremely useful as drugs such as antiinflammatory, analgesic and antiallergic agents.

What is claimed is:

1. An inhibitor of kallikrein formation extracted from infected tissue inoculated with a poxvirus, and which is a hygroscopic powder, pale yellowish brown in appearance, soluble in water, methanol and acetone and insoluble in benzene and ether, has a molecular weight greater than 1,000 but less than 20,000 and an ultraviolet adsorption of $\lambda max = 265–275$ nm and which gives a positive color reaction for amino acid, sugar and phosphorus, and a negative color reaction for protein and phenol.

2. A process for preparation of the inhibitor of kallikrein formation of claim 1, which comprises extracting infected tissue inoculated with a poxvirus, deproteinizing the extract, mixing the deproteinized extract with an adsorbent, eluting the adsorbed material from the adsorbent, and fractionating the eluate to obtain a fraction having a molecular weight greater than 1,000 but less than 20,000.

3. The process according to claim 2, wherein the poxvirus is vaccinia virus.

4. The process according to claim 2, wherein rabbit's skins are used as the infected tissue.

5. The process according to claim 3, wherein the mixing of the deproteinized extraction and an adsorbent is carried out at a pH in the range 3.5–5.5.

6. The process according to claim 3, wherein the elution of the adsorbed material from the adsorbent is carried out at a pH in the range of 9–12.

7. The process according to claim 3, wherein the eluted material from the adsorbent is fractionated by ultrafiltration.

8. An antiinflammatory, analgesic or antiallergic composition comprising an effect amount of the inhibitor of kallikrein formation according to claim 1 and a pharmaceutically acceptable carrier.

* * * * *